US00PP28987P2

(12) United States Plant Patent
Craigie

(10) Patent No.: US PP28,987 P2
(45) Date of Patent: Feb. 20, 2018

(54) ***AGAPANTHUS* PLANT NAMED 'PMB012'**

(50) Latin Name: *Agapanthus orientalis*
Varietal Denomination: PMB012

(71) Applicant: John Maxwell Craigie, Pine Mountain (AU)

(72) Inventor: John Maxwell Craigie, Pine Mountain (AU)

( * ) Notice: Subject to any disclaimer, the term of this patent is extended or adjusted under 35 U.S.C. 154(b) by 0 days.

(21) Appl. No.: 15/530,103

(22) Filed: Dec. 1, 2016

(51) Int. Cl.
*A01H 5/02* (2006.01)

(52) U.S. Cl.
USPC ..... Plt./398

(58) Field of Classification Search
USPC ..... Plt./398
See application file for complete search history.

(56) References Cited

PUBLICATIONS https://www.pinemountainnursery.com.au/news/15/Agapanthus-PMB012-Maxsie%E2%84%A2-%252d-New-Release.html Dec. 12, 2015.*

* cited by examiner

*Primary Examiner* — Annette H Para
(74) *Attorney, Agent, or Firm* — Cassandra Bright

(57) ABSTRACT

A new and distinct *Agapanthus* cultivar named 'PMB012' is disclosed, characterized by bi-color blue and white flowers. Flowers can be standard 6 tepaled, or having up to 12 tepals. Flowering begins early to mid Summer. Plants are distinctively compact with upright foliage and a mature height near 50 cm. The new variety is an *Agapanthus*, typically produced as an outdoor ornamental plant.

2 Drawing Sheets

Figure 1:
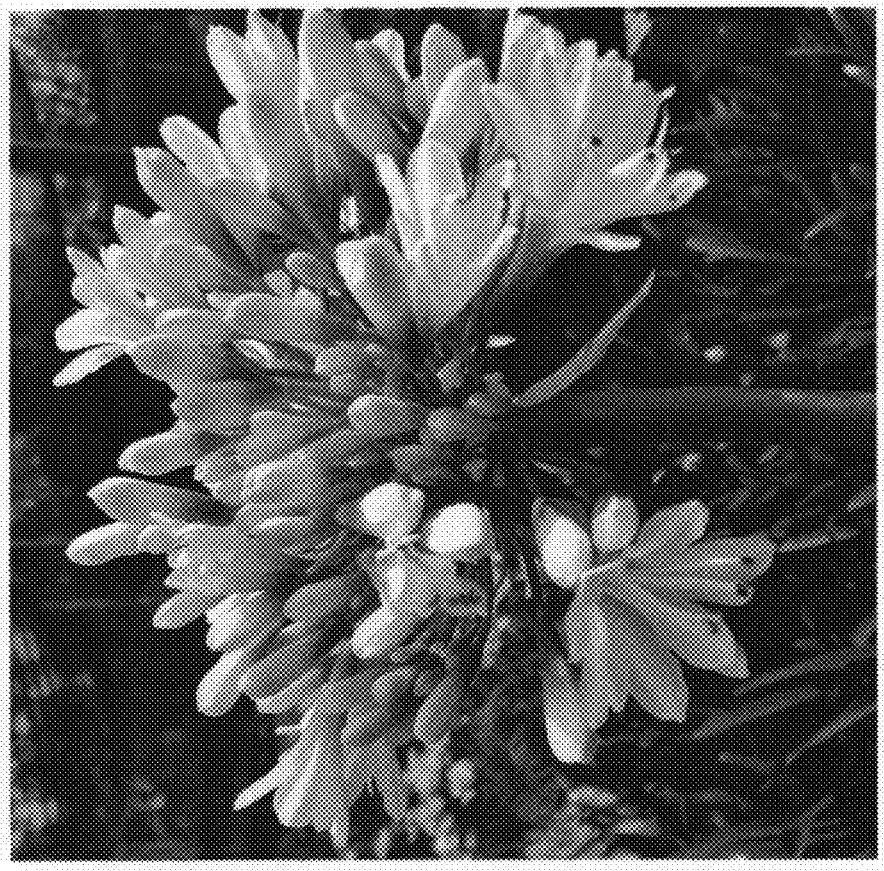

Latin name of the genus and species: *Agapanthus orientalis*.

Variety denomination: 'PMB012'.

BACKGROUND OF THE INVENTION

The new cultivar is the product of a controlled breeding program with the objective to produce new *Agapanthus orientalis* varieties with bi-color flowers, moderate plant heights which are easy to propagate. The new variety is the result of the self-pollination of an unpatented, proprietary *Agapanthus orientalis* developed as part of the breeding program. The self-pollination resulting in the new variety was conducted during 2008.

The new variety was selected by the inventor at a research nursery in Pine Mountain, Australia in January 2011. After identifying the interesting new plant, the inventor divided the original plant and subsequent propagules over several years, to establish stability.

Asexual reproduction of the new cultivar 'PMB012' was first performed by division in Pine Mountain, Australia, during Spring 2011, on a very limited basis. Access to all plants was restricted, as plants were kept in a location not open to the public, at the inventor's nursery. Through subsequent propagation, multiple generations have been reproduced, which have shown that the unique features of this cultivar are stable and reproduced true to type.

SUMMARY OF THE INVENTION

The cultivar 'PMB012' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PMB012'. These characteristics in combination distinguish 'PMB012' as a new and distinct *Agapanthus* cultivar:

1. Violet-blue and white bi-color flowers.
2. Distinctively small individual flowers.
3. Compact foliage.
4. Vigorous growth and ease of propagation.
5. Flowering begins mid to late Summer.
6. Flowering occurs in less than 12 months from potting a rooted plantlet.
7. Individual flowers may be single, with 6 tepals, or having up to 12 tepals.

PARENT COMPARISON

Plants of the new cultivar 'PMB012' are similar to the parent in most horticultural characteristics. However, the new variety is differs in the following:

1. Mature height to 50 cm, the parent variety has a mature height of 120 cm.
2. Individual flowers are multi-tepaled, as well as standard 6 tepaled. The parent variety flowers are all standard 6-tepaled.
3. The new variety has broad, erect foliage, the parent variety has arching foliage.
4. The new variety seeds seed infrequently and small quantities, the parent variety sets seed more regularly and in greater abundance.

COMMERCIAL COMPARISON

Plants of the new cultivar 'PMB012' are similar to the unpatented commercial variety *Agapanthus orientalis*

'PMB011', U.S. Plant Pat. No. 26,475 in most horticultural characteristics. The new variety, however, differs in the following:

1. Flowering begins mid to late Summer, the comparator begins flowering early to mid-Spring.
2. 'PMB012' produces flowers with more than 6 tepals, as well as 6 tepaled flowers. The comparator only produces flowers with 6 tepals.
3. The new variety seeds seed infrequently and small quantities, this comparator variety sets seed more regularly and in greater abundance.
4. Foliage of the new variety is wider.
5. Peduncles of the new variety are shorter.

Plants of the new cultivar 'PMB012' are similar to the commercial variety *Agapanthus praecox orientalis* 'PMN06', U.S. Plant Pat. No. 24,651, in most horticultural characteristics. The new variety, however, differs in the following:

1. Mature height to 50 cm, this comparator variety has a mature height of 120 to 150 cm.
2. Individual flowers are multi-tepaled, as well as standard tepaled. This comparator variety flowers are all standard non multi-tepaled.

BRIEF DESCRIPTION OF THE PHOTOGRAPHS

The accompanying photograph in FIG. 1 illustrates in full color a close up of the inflorescence of 'PMB012'.

Figure 2:
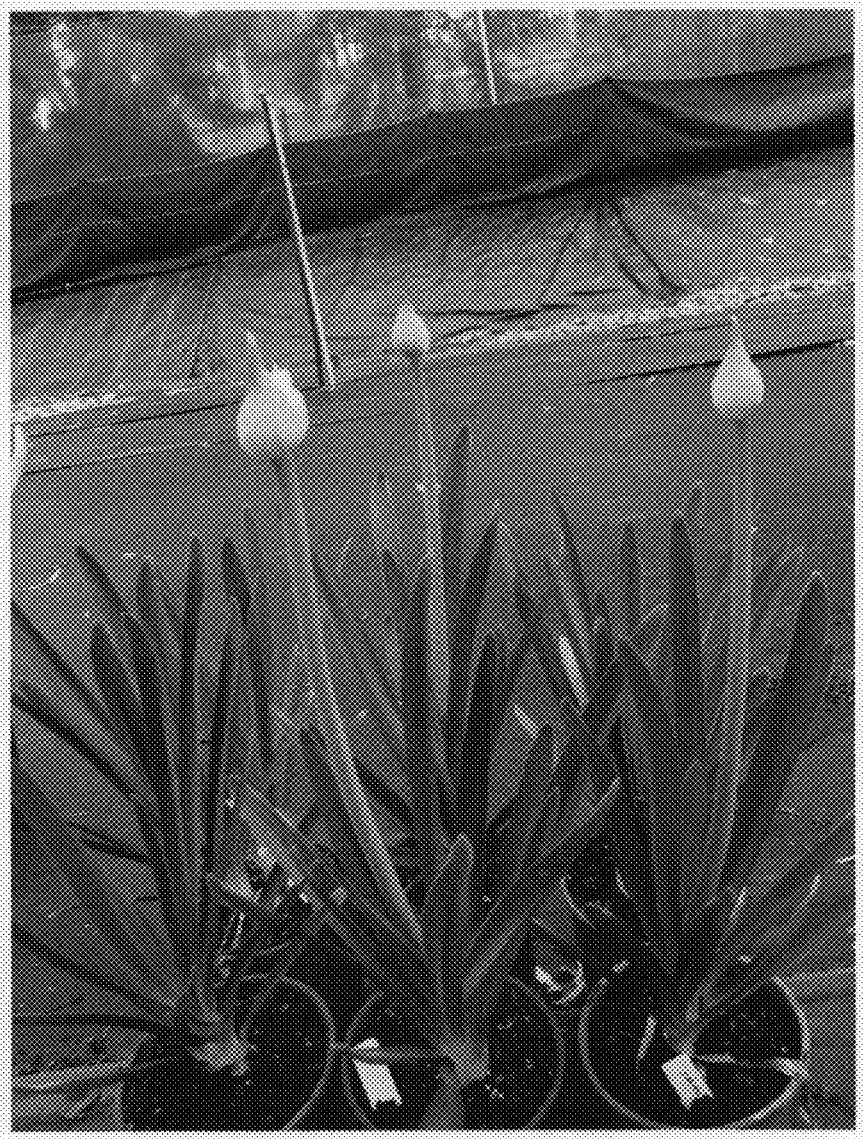

FIG. 2 illustrates in full color typical plants of 'PMB012' at approximately 10 months of age from a rooted plug.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'PMB012' plants grown outdoors in Pine Mountain, Australia. Plants are approximately 1 year old, measurements taken in January. Temperatures over the course of the year ranged from approximately 3° C. to 27° C. at night and 3° C. to 38° C. during the day. No artificial light, photoperiodic treatments were given to the plants. No chemical treatments were given to plants. Measurements and numerical values represent averages of typical plant types.

Botanical classification: *Agapanthus orientalis* 'PMB012'.

PROPAGATION

Root description: Thick, fleshy root system colored near Greyed-Orange 164D and Orange-White 159C.

PLANT

Container size and age: 14 cm, approximately 10 months.

Growth habit: Clump forming tender perennial with upright foliage.

Height: Foliar plane 38 cm. Flowering plane approximately 48 cm.

Plant spread: Approximately 30 cm.

Growth rate: Moderate.

FOLIAGE

Leaf:

*Average leaf length*.—Average 20 cm.

*Average leaf width*.—Average 4.0 cm.

*Arrangement*.—Basal, irregular whorls.

*Shape of blade*.—Linear.

*Apex*.—Acute.

*Base*.—Cuneate.

*Margin*.—Entire.

*Texture of top surface*.—Smooth.

*Texture of bottom surface*.—Smooth.

*Quantity of leaves per plant*.—Average 40 to 55.

*Color*.—Mature and young foliage is the same color. Upper blade: Near Green 143A. Lower Blade: Near Green 143A.

*Venation*.—Type: Linear. Venation color upper side: Indistinguishable from leaf blade. Venation color under side: Indistinguishable from leaf blade.

FLOWER

Natural flowering season: Beginning in early to mid Summer, lasting until Fall in temperate Australia.

Length of flowering period: Approximately 9 to 12 weeks.

Inflorescence type: Terminal Umbel with approximately 40 to 50 individual flowers and approximately 10 to 20 buds. Approximately 4 to 12 umbels produced during the peak flowering season.

Individual flower type: Both single, having 6 tepals and multi-tepaled flowers within the same inflorescence.

Flower profile: Funnelform.

Bud:

*Shape*.—Ovate.

*Shape*.—Narrow ovate.

*Length*.—Approximately 1.2 cm.

*Diameter*.—Approximately 0.7 cm.

*Color*.—Near White 155A, base flushed Violet-Blue 94C.

Umbel size:

*Diameter*.—Average 18 cm.

*Height*.—Average 10 cm.

Corolla:

*Arrangement*.—Apetalous, single, and double campanulate flowers composed of 6 to 12 basally fused tepals, shaped into a flared trumpet.

*Size*.—Length: Approximately 2.8 cm. Width: Approximately 1.5 cm at widest point. Lobe Length: Approximately 1.8 cm. Lobe Width: Average 0.7 cm.

*Margin*.—Entire.

*Shape*.—Lanceolate.

*Apex*.—Broadly acute.

*Texture*.—Glabrous all surfaces.

Color:

*Tepals*.—When opening: Outer surface: Near White N155A, base flushed Violet-Blue 94C. Inner surface: Near White N155A, base flushed Violet-Blue 94C. Fully opened: Outer surface: White N155A, base flushed Violet-Blue 94C. Inner surface: White N155A, base flushed Violet-Blue 94C.

*Sepals*.—Not Present.

Fragrance: Faint musty scent.
Pedicels:
*Length*.—Average range 1 to 1.5 cm.
*Width*.—Approximately 0.2 cm.
*Aspect*.—Mainly straight.
*Color*.—Near RHS Green 143A.
Scape:
*Length*.—Average 38 cm.
*Width*.—Approximately 1.2 cm.
*Angle*.—Upright from center of plant, mainly straight, with very slight curvature.
*Strength*.—Very strong.
*Color*.—Near RHS Green 137A, very slightly flushed near Greyed-Purple N186A.
Flower filament color: Near White N155A.
Flower anther color: Near Violet N92A.
Flower style color: Near White N155A.

REPRODUCTIVE ORGANS

Stamens:
*Number*.—Average 6.
*Filament length*.—Approximately 2.1 cm.
*Filament color*.—Near White N155A.
*Anther length*.—0.2 cm.
*Anther color*.—Near Violet N92A.
*Pollen*.—Scant, colored near Violet-Blue 91C.
Pistil:
*Number*.—1.
*Length*.—Approximately 2.8 cm.
*Style color*.—Near White N155A.
*Stigma*.—Shape: Linear. Color: Near RHS White N155A.
*Ovary color*.—Near RHS Yellow-Green 145B.

OTHER CHARACTERISTICS

Seed production: Scant seed production. Black seeds, oblong, approximately 1 cm long by 6 mm wide.
Disease resistance: Neither resistance nor susceptibility to normal diseases and pests of *Agapanthus*.
Temperature tolerance: Typically USDA zones 7b through 11.
Drought tolerance: Will tolerate considerable dryness once established.

What is claimed is:

1. A new and distinct cultivar of *Agapanthus* plant named 'PMB012' as herein illustrated and described.

* * * * *